(12) United States Patent
Xu et al.

(10) Patent No.: US 11,293,890 B2
(45) Date of Patent: Apr. 5, 2022

(54) MULTI-ENZYMATIC BIOSENSORS AND STABILIZATION OF MULTI-ENZYMATIC BIOSENSORS AT ROOM TEMPERATURE

(71) Applicant: Instrumentation Laboratory Company, Bedford, MA (US)

(72) Inventors: Xiaoxian Xu, Maynard, MA (US); Prasad Pamidi, Burlington, MA (US); Jose Cervera, Arlington, MA (US)

(73) Assignee: Instrumentation Laboratory Company, Bedford, MA (US)

( * ) Notice: Subject to any disclaimer, the term of this patent is extended or adjusted under 35 U.S.C. 154(b) by 273 days.

(21) Appl. No.: 16/429,922

(22) Filed: Jun. 3, 2019

(65) Prior Publication Data

US 2020/0319134 A1 Oct. 8, 2020

Related U.S. Application Data

(60) Provisional application No. 62/830,191, filed on Apr. 5, 2019.

(51) Int. Cl.
*G01N 27/327* (2006.01)
*C12Q 1/00* (2006.01)
(Continued)

(52) U.S. Cl.
CPC ......... *G01N 27/3275* (2013.01); *C12Q 1/002* (2013.01); *C12Q 1/003* (2013.01); *C12Q 1/005* (2013.01); *C12Q 1/54* (2013.01); *G01N 27/308* (2013.01); *G01N 27/3272* (2013.01); *G01N 27/3276* (2013.01); *G01N 27/3335* (2013.01); *G01N 33/5308* (2013.01); *G01N 33/70* (2013.01); *G01N 33/96* (2013.01); *G06F 17/18* (2013.01); *G16B 25/30* (2019.02); *G16H 10/40* (2018.01); *C12Q 1/58* (2013.01); *G01N 27/3274* (2013.01); *G01N 33/5438* (2013.01); *G06F 30/331* (2020.01)

(58) Field of Classification Search
CPC ...... G01N 27/327–3272; C12Q 1/0001; C12Q 1/0005
See application file for complete search history.

(56) References Cited

U.S. PATENT DOCUMENTS 6,071,392 A * 6/2000 Yamamoto ............. C12Q 1/005
  204/403.08
6,767,441 B1 * 7/2004 Cai ........................ C12Q 1/004
  204/403.03
(Continued)

FOREIGN PATENT DOCUMENTS

EP   1753872 B1   1/2014
JP   2004-528579 A   9/2004
(Continued)

OTHER PUBLICATIONS

International Search Report and Written Opinion for International Application No. PCT/US2019/035152, dated Nov. 8, 2019, 12 pages.
(Continued)

*Primary Examiner* — Alexander S Noguerola
(74) *Attorney, Agent, or Firm* — Burns & Levinson LLP

(57) ABSTRACT

Disclosed are multi-enzyme biosensors that are stable at ambient temperature, and methods of making thereof.

34 Claims, 6 Drawing Sheets

(51) Int. Cl.
    *G01N 27/333*     (2006.01)
    *G01N 33/70*     (2006.01)
    *G01N 33/96*     (2006.01)
    *G01N 27/30*     (2006.01)
    *C12Q 1/54*     (2006.01)
    *G01N 33/53*     (2006.01)
    *G16H 10/40*     (2018.01)
    *G16B 25/30*     (2019.01)
    *G06F 17/18*     (2006.01)
    *C12Q 1/58*     (2006.01)
    *G01N 33/543*     (2006.01)
    *G06F 30/331*     (2020.01)

(56) References Cited

U.S. PATENT DOCUMENTS

| | | | |
|---|---|---|---|
| 6,960,466 | B2 | 11/2005 | Pamidi et al. |
| 7,285,198 | B2 * | 10/2007 | Douglas .............. B82Y 30/00 |
| | | | 204/400 |
| 7,632,672 | B2 | 12/2009 | Pamidi et al. |
| 7,815,788 | B2 | 10/2010 | Schaffar et al. |
| 8,426,192 | B2 | 4/2013 | Pamidi et al. |
| 9,487,811 | B2 | 11/2016 | Zhao et al. |
| 2004/0163949 | A1 | 8/2004 | Sorensen |
| 2004/0211666 | A1 * | 10/2004 | Pamidi .............. C12Q 1/005 |
| | | | 204/403.01 |
| 2004/0256227 | A1 | 12/2004 | Shin et al. |
| 2006/0275857 | A1 | 12/2006 | Kjaer et al. |
| 2007/0034512 | A1 | 2/2007 | Yamaoka |
| 2007/0131548 | A1 * | 6/2007 | Winarta .............. C12Q 1/005 |
| | | | 204/403.02 |
| 2008/0173064 | A1 | 7/2008 | Schaffar et al. |
| 2013/0186755 | A1 | 7/2013 | Chu |
| 2017/0254771 | A1 | 9/2017 | Balasubramanian et al. |

FOREIGN PATENT DOCUMENTS

| | | | |
|---|---|---|---|
| JP | 2005501254 | A | 1/2005 |
| JP | 2008502921 | A | 1/2008 |
| JP | 2011508221 | A | 3/2011 |
| JP | 2014-153243 | A | 8/2014 |
| WO | 98/21356 | A1 | 5/1998 |
| WO | WO 98/21356 | A * | 5/1998 .............. C12Q 1/00 |
| WO | 03/019171 | A1 | 3/2003 |
| WO | 2005/052596 | A1 | 6/2005 |
| WO | 2008/028011 | A2 | 3/2008 |
| WO | 2009/053370 | A1 | 4/2009 |
| WO | WO 2009/053370 | A1 * | 4/2009 .............. C12Q 1/00 |
| WO | 2009/082699 | A1 | 7/2009 |
| WO | 2016/096725 | A1 | 6/2016 |

OTHER PUBLICATIONS

International Search Report and Written Opinion for International Application No. PCT/US2019/035155, dated Nov. 14, 2019, 12 pages.
International Search Report and Written Opinion for International Application No. PCT/US2019/035156, dated Sep. 20, 2019, 12 pages.
Hydrourethane AdvanSource Biomaterials, Advancesource Biomaterials, Jun. 21, 2011 [retrieved on Sep. 19, 2019]. Retrieved from the Internet URL: http://www.advbiomaterials.com/pdf/HydroThane%20Factsheet.pdf.
International Search Report and Written Opinion for International Application No. PCT/US2019/035157, dated Dec. 12, 2019, 18 pages.
International Search Report and Written Opinion for International Application No. PCT/US2019/035153, dated Nov. 26, 2019, 12 pages.
International Preliminary Report on Patentability dated Sep. 28, 2021, International Application No. PCT/US2019/036156 filed Jun. 3, 2019 (7 pages).
Notice of Reasons for Rejection for Japanese Patent Application No. 2020-571701, dated Sep. 2, 2021, (with English translation), 18 pages.
Nichols et al., The effect of nitric oxide surface flux on the foreign body response to subcutaneous implants, Biomaterials, vol. 33, No. 27, May 20, 2012, pp. 6305-6312.
Conway et al., Layer-by-layer design and optimization of xerogel-based amperometric first generation biosensors for uric acid, Journal of Electroanalytical Chemistry, vol. 775, May 25, 2016, pp. 135-145.
Tjell et al., Diffusion rate of hydrogen peroxide through water-swelled polyurethane membranes, Sensing and Bio-Sensing Research, vol. 21, No. 27, Nov. 1, 2018, pp. 35-39.
Hydrourethane AdvanSource Biomaterials, Advancesource Biomaterials, Jun. 21, 2011 [retrieved on Sep. 19, 2019]. Retrieved from the Internet URL: http://advbiomaterials.com/pdf/HydroThane%20Factsheet.pdf.
Hydromed D Series, Advancesource Biomaterials, Apr. 16, 2010, [retrieved on Sep. 20, 2019]. Retrieved from the Internet URL: http://www.advbiomaterials.com/products/hydrophilic/HydroMed.pdf.
Notice of Reasons for Rejection for Japanese Patent Application No. 2020-571761, dated Dec. 24, 2021, (with English translation), 14 pages.
Examiner Requisition for Canadian Patent Application No. 3,104,896, mailed Feb. 18, 2022, 5 pages.
Communication pursuant to Rules 161(1) and 162 EPC for European Patent Application No. 19734964.0, dated Dec. 1, 2021, 3 pages.

* cited by examiner

MULTI-ENZYMATIC BIOSENSORS AND STABILIZATION OF MULTI-ENZYMATIC BIOSENSORS AT ROOM TEMPERATURE

CROSS REFERENCE TO RELATED APPLICATIONS

This application claims priority to and benefit of U.S. Provisional Application No. 62/830,191, filed Apr. 5, 2019 and is incorporated in its entirety herein for all intents and purposes.

FIELD OF THE INVENTION

The present invention relates to multi-enzyme biosensors such as creatine and creatinine biosensors and methods of making thereof, having enzyme stability at room temperature and prolonged shelf-life and use-life.

BACKGROUND

Enzyme biosensors are used to detect numerous analytes such as creatinine, creatine, glucose, urea and lactate, in a patient body fluid sample such as blood. As such, enzyme biosensors are particularly important in assisting point-of-care diagnosis of a patient malady.

However, one of the drawbacks of enzyme biosensors, particularly in point-of care applications, is loss of enzyme activity over its continuous use and over its shelf-life at ambient temperature, typically less than 15 days. Thus, short shelf-life is a critical factor limiting the practical application of enzyme biosensors such as the creatine and the creatinine biosensors.

The shelf-life of the enzyme biosensors that is particularly problematic is the creatinine biosensor. Measurement of creatinine is helpful for determining kidney dysfunction in a patient, for example.

The creatinine sensor is unusual at least because it is an enzymatic biosensor containing not merely one, but three enzymes. These three enzymes are immobilized on the surface of an electrode through a crosslinking reagent, for example, glutaraldehyde, or by physical absorption, entrapment with a hydrogel, or coated on the electrode by electropolymerization with conductive monomers, for example. Creatinine detection in a creatinine biosensor is based on a three enzyme cascading reaction as follows:

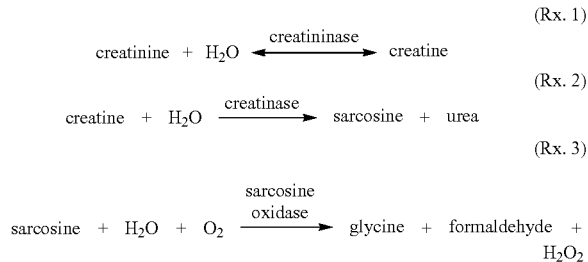

The product generated following the three enzyme cascading reaction is hydrogen peroxide ($H_2O_2$). Hydrogen peroxide is then electrochemically detected on the electrode under a constant polarization potential.

For the commercialization and practical application of the above described creatinine and creatine biosensors in accurately measuring biological sample over the long term, meaning 5 months to a year or more, a major challenge that has to be overcome is long term stability of the enzymes during storage (shelf-life) of the biosensor at ambient temperatures in the range of 15-25° C., preferably 18-24° C., more preferably 20-24° C., and 24° C.

From a design principle, the sensor sensitivity (slope) towards measuring the substrate creatinine is directly related to the remaining enzyme activity of the immobilized enzyme mixture on the electrode of the biosensor. The three enzymes, creatininase, creatinase and sarcosine oxidase, are very delicate and are not stable at ambient temperature. The fast decay of the creatinine biosensor sensitivity (slope) due to protein denaturation is the basis for its instability and very limited use-life or shelf-life.

Due to the presence of creatine in clinical samples, aqueous quality control reagents, calibration reagents, an additional sensor for creatine measurement is required for correcting the creatine response of the creatinine sensor. Creatine sensors contain two enzymes and involve the second and third steps of the enzyme cascade reactions illustrated above.

Whole blood analyzers, for example the GEM Premier® analyzer (Instrumentation Laboratory Company, Bedford, Mass.) utilize a multi-use, single consumable cartridge for example, the cartridges described in U.S. Pat. No. 6,960,466 assigned to Instrumentation Laboratory Company (Bedford, Mass.) and incorporated by reference herein in its entirety for all intents and purposes. The cartridge contains all critical components (sensor arrays, reference solutions, rinse solutions and calibration reagents) including multi-enzyme sensors, for example, creatinine and creatine sensors, for blood measurement of blood analytes and require ambient temperature storage for a minimum of 5 months.

Most commercially available creatinine sensors with similar general design in the prior art address the problem of short creatinine sensor use-life and shelf-life by refrigeration of the critical parts of the biosensor to extend its life. However, this approach adds complexity to instrument operation by the field operator at point-of-care locations of the hospital, for example. For the GEM® PAK cartridge (Instrumentation Laboratory Company, Bedford, Mass.), for example, biosensors are an integral and critical feature of the cartridge. It is impractical to store the entire cartridge in refrigeration due to cartridge size and reagent stability, for example, reagent stability of the reference solution and stabilization of gases $pO_2$ and $pCO_2$ of calibration solutions.

It is known that the activity of a single enzyme either in solution or in dry stage at free form can be extended with mono- or poly-saccharides. However, extending the activity of a three or two enzyme biosensor system at dry storage and ambient temperature for a useful shelf-life introduces challenges not encountered in extending the activity of a single enzyme biosensor system. The invention described below identifies and solves the problem of extending the activity, shelf-life and use-life of a multi-enzyme biosensor such as the creatine and creatinine biosensors.

Maintaining enzyme activity in an enzymatic biosensor is critical to shelf-life and use-life. It is hypothesized that in the presence of water, polyhydroxyl groups contained in a sugar complex with water. When the sugar-water complex interacts with an enzyme, the sugar-water complex penetrates into the enzyme structure even when the enzyme is crosslinked. Without being bound to theory, it is believed that sugar complexed with water reduces unfolding of the enzyme structure which assists in maintaining enzyme activity.

However, compared to maintaining stability of a single enzyme sensor, having three enzymes together in a creatinine sensor presents more challenges to maintaining enzyme stability due to the complex interactions among the multiple enzyme chemical structures. These complex interactions cause instability of one or more enzymes during preparation of the sensors or during shelf storage. These interactions lead to less than expected biosensor performance. The aim of the invention disclosed herein is to address the lack of stability and useful shelf-life of biosensors, such as the creatinine and creatine multi-enzyme sensors, due to cross interactions of the enzymes causing undesirable reduction in shelf-life and use-life of the sensors at ambient temperatures in the range of 15-25° C.

SUMMARY OF THE INVENTION

The present invention relates to stable multi-enzyme biosensors at room temperature, methods of making, and cartridges housing the stable multi-enzyme biosensors. The terms sensor and biosensor are used interchangeably throughout.

In one aspect, the invention is directed to a method for making the multi-enzyme biosensor, the biosensor having stability for at least 5 months shelf-life at ambient temperature and an additional three weeks use-life. The method comprises providing an electrode, casting a plurality of enzymes in solution, i.e., an enzyme mixture, on the surface of the electrode to form an enzyme layer, applying a diffusion barrier on the surface of the enzyme layer, applying a polysaccharide solution to the electrode, and drying the electrode to form the stable multi-enzyme biosensor.

The electrodes of the biosensor, are selected, for example, from the group consisting of platinum, gold, palladium, alloys of platinum, gold and palladium, carbon, graphite and carbon nanotubes.

The plurality of enzymes are selected from but not limited to the group consisting of creatininase, creatinase, and sarcosine oxidase. In one embodiment of the invention the enzymes are immobilized on the electrode by chemical cross-linking, for example, with glutaraldehyde, 1,4-diisocyanatobutane, 1,2,7,8-diepoxyoctane and 1,2,9,10-diepoxydecane, or combinations thereof. The biosensor is capable of measuring creatine and/or creatinine in a body fluid sample such as blood, plasma or serum.

The step for applying a polysaccharide solution to the electrode in various embodiments includes applying one or more polysaccharides such as but not limited to the disaccharides, sucrose, trehalose, and lactitol, the trisaccharide, raffinose, and other polysaccharides. The polysaccharide may be added to the enzyme mixture before the electrode is solvent cast with the enzyme mixture, or, in a solution after application of the diffusion barrier to the electrode, or as a combination of the above steps. The electrode may be immersed in a polysaccharide solution, dried, and re-immersed in the polysaccharide solution a plurality of times followed by drying each time. The concentration of the polysaccharide in solution is in the range of greater than 0% to about 25% and the duration of polysaccharide treatment is thirty minutes or longer.

In one embodiment of the invention, a polyionic compound selected from the group consisting of polyethylenimine, poly(N-vinylimidazole), polypropyleneimine, polyallylamine, polyvinylpiridine, polyvinylpyrollidone, polylysine, protamine, and derivatives of the polyionic compounds may be added to the enzyme mixture.

Application of the diffusion barrier comprises applying a polymeric compound selected from the group consisting of polyurethane, poly(tetrafluoroethylene) ionomers (the perfluorosulfonate ionomer, NAFION®), poly-(2-hydroxymethyl methacrylate), polyvinyl chloride, cellulose acetate, and mixtures and copolymers thereof to the electrode to form the outer membrane that is in contact with the body fluid sample introduced in a body fluid sample flow chamber in which one or more of creatine and creatinine are to be measured. The enzyme layer is positioned between the outer membrane and the electrode.

A stable multi-enzyme biosensor according to the method of the invention maintains stable creatinine performance of greater than 400 pA/mg/dl after at least 5 months storage at ambient temperature and 21 days of use.

In another aspect, the invention is directed to a multi-enzyme biosensor comprising an electrode, a plurality of enzymes immobilized on the electrode as an enzyme layer, a diffusion barrier on the surface of the enzyme layer, and a polysaccharide. The electrodes, enzymes, cross-linkers, polysaccharides, diffusion barriers, and stability of the multi-enzyme biosensors are described above.

In yet another aspect, the invention is directed to a cartridge housing at least one multi-enzyme sensor in a sensor array, the at least one multi-enzyme sensor comprising an electrode with an enzyme layer comprising, a plurality of enzymes, a diffusion barrier on the surface of the enzyme layer of the electrode adjacent a body fluid sample flow chamber, and a polysaccharide. The multi-enzyme sensor comprising electrodes, enzymes, cross-linkers, polysaccharides, diffusion barriers, and stability of the multi-enzyme biosensors are described above. In one embodiment according to the invention, in addition to a card having a sensor array in which the enzyme biosensor according to the invention is included, the cartridge houses at least one multi-enzyme sensor described above in the sensor array, and additionally includes reference solutions, fluidic channels, calibration reagents, rinse solutions and electronic components for operatively interfacing with a clinical analyzer, and other critical components.

Figure 4A:
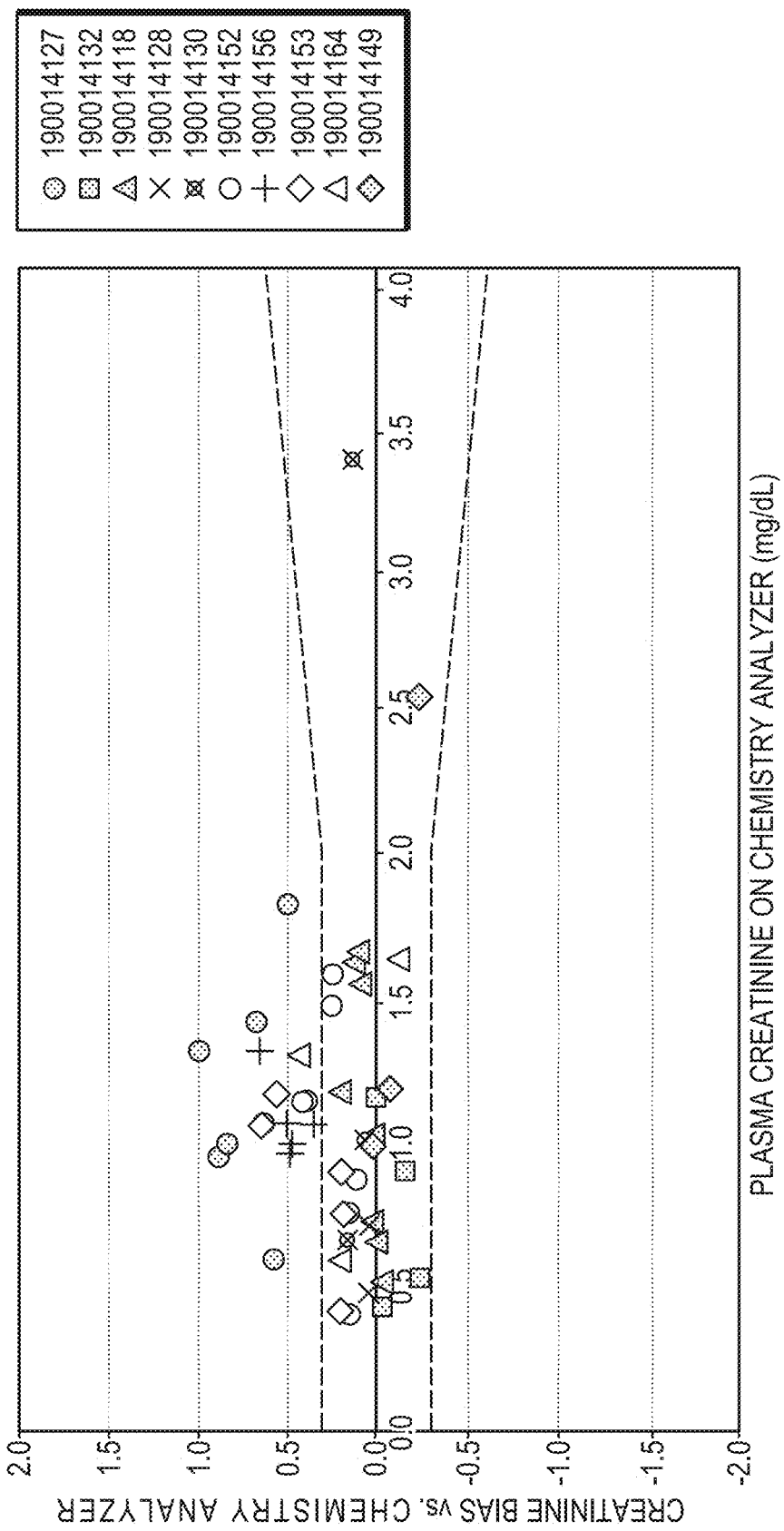

FIG. 4A is a graphic illustration of creatinine sensor analytical performance in clinical samples in a group of ten cartridges, each represented by a different symbol, of creatinine and creatine sensors without polyethylenimine in the enzyme mixture. The difference (aka bias, or error) of creatinine measured between GEM PAK and a reference chemistry analyzer were plotted vs. plasma creatinine reported by the reference chemistry analyzer, the dashed lines were acceptable limits of bias at any given creatinine concentration for clinical applications. Due to sensor-to-sensor variation in performance, the bias between GEM and reference analyzers were scattered and many samples had bias exceeded the acceptable limits (data points outside dashed lines).

Figure 4B:
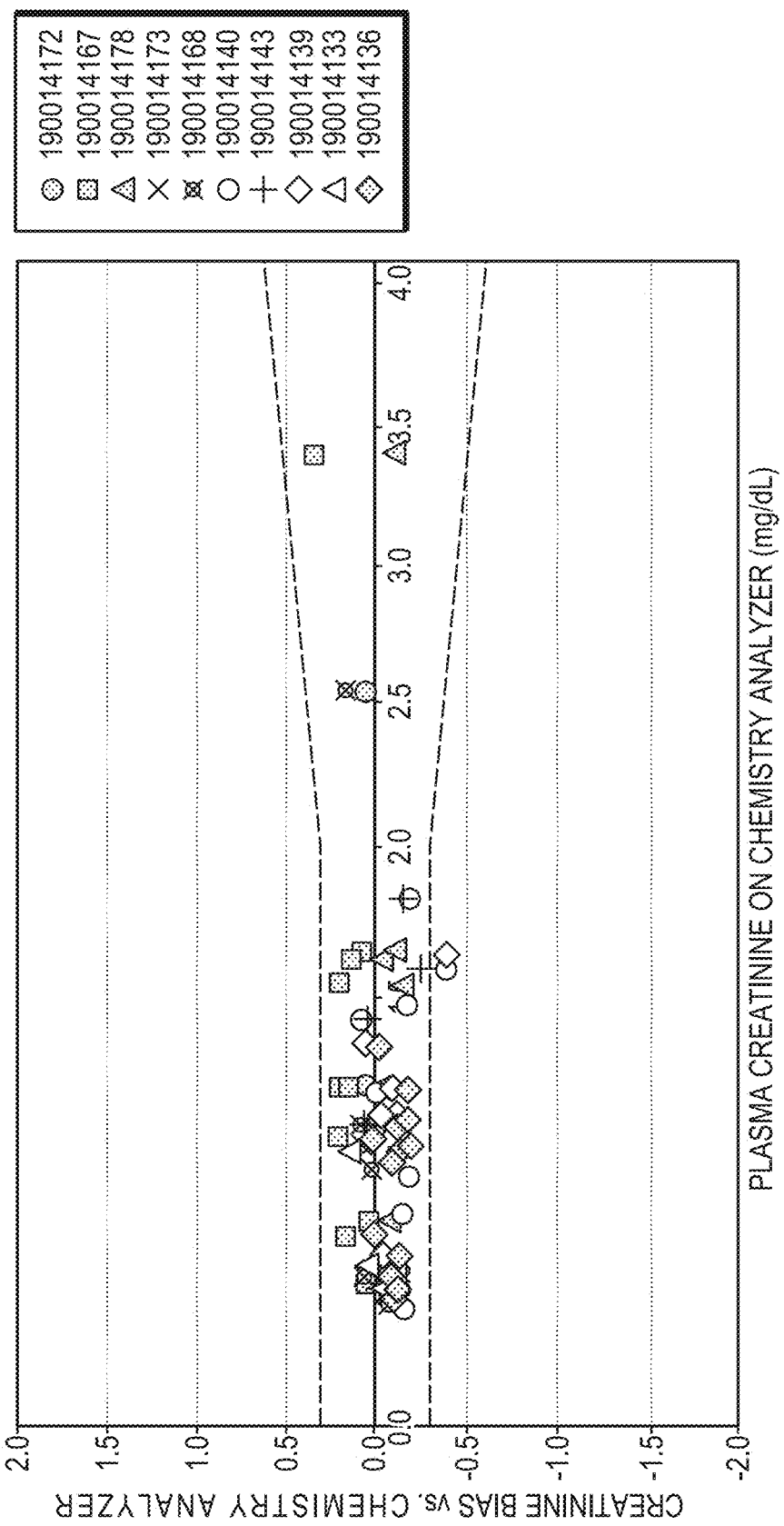

FIG. 4B is a graphic illustration of creatinine sensor analytical performance in clinical samples in another group of ten cartridges, each represented by a different symbol, of creatinine and creatine sensors with polyethylenimine-containing enzyme mixture. The difference of creatinine measured between GEM PAK and a reference chemistry analyzer were plotted vs. plasma creatinine reported by the reference chemistry analyzer. The dashed lines were acceptable limits of bias at any given creatinine concentration for clinical applications. With improved sensor performance, the biases were tightly distributed and most of the samples had bias within the clinical acceptable limits (data points within dashed lines).

DETAILED DESCRIPTION

The inventions described below are directed to a device and related method for enhancing enzyme stability extending the shelf-life and use-life of multi-enzyme biosensors including but not limited to creatine and creatinine biosensors used in clinical analyzers for in vitro diagnostics, point-of-care applications in particular.

According to the invention, polysaccharides, for example, disaccharides, such as sucrose, are optimal compositions for preserving the stability and activity and extending the shelf-life and use-life of a multi-enzyme system such as a three-enzyme biosensor system for example, the creatinine sensor. Other poly-saccharides such as trehalose (α-D-Glucopyranosyl-α-D-glucopyranoside), raffinose (O-α-D-Galactopyranosyl-(1→6)-α-D-glucopyranosyl β-D-fructofuranoside), and lactitol (4-O-β-D-Galactopyranosyl-D-glucitol) (all poly-saccharides obtained from Sigma) also improve stability and activity of enzymes in multi-enzyme biosensors extending their shelf-life and use-life.

For simplicity, 10% sucrose was used as an example polysaccharide for the studies presented below. Significant improvement in maintaining multi-enzyme activity at ambient temperature was observed with sucrose stabilization. A stable shelf-life of at least 5 months was achieved when the multi-enzyme sensor was stored at room temperature following sucrose-treatment enzyme stabilization.

Polyelectrolytes, i.e., polyionic compounds, in addition to polysaccharides are another known class of chemicals useful as a multi-enzyme stabilizer, for example, polyethylenimine (PEI). PEI has been applied in single enzyme biosensors, e.g., lactate enzymatic sensor formulation on biosensor-containing cartridges, for example, GEM®-PAK (Instrumentation Laboratory Company; Bedford, Mass.) for that purpose. To further enhance the sucrose stabilization effect on a three-enzyme or a two enzyme biosensor system, a polyelectrolyte/sugar stabilization system was studied by introducing PEI into the three-enzyme mixture. The formulation, discussed below, has been optimized to achieve the best results, i.e., maintaining sensor slope above 400 pA/mg/dL after 5 month dry storage and three weeks of use life. PEI improves enzyme stability through its electrostatic interaction with the enzyme(s) outer shell protein structure, and may further facilitate the penetration of sucrose-water complex into the three dimensional structure of the immobilized enzyme. Thus, the immobilized enzyme system in the presence of PEI is packed with the polyhydroxyl compound, sucrose, for example, instead of free water, and maintains stable activity of the enzymes during the drying process at the sensor manufacturing step and throughout the dry storage during the shelf-life prior to use at the clinical site.

As described below, it was determined by the inventors that a disaccharide, for example, sucrose, is one of the optimal compositions for preservation and stability of the activity of a two or three-enzyme system for a biosensor, for example, a creatinine sensor. Other polysaccharides such as trehalose, raffinose, and lactitol also have similar effect on multi-enzyme sensors improving stability.

Figure 1:
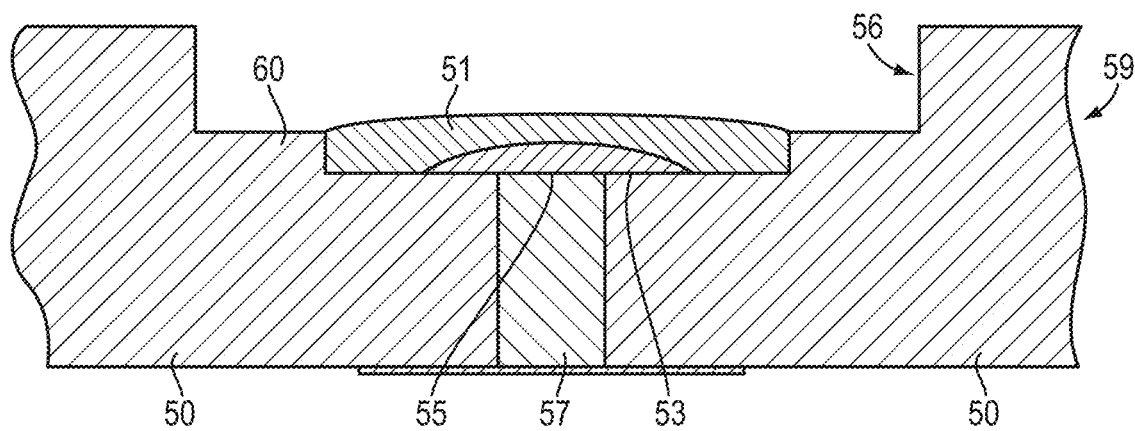
FIG. 1 illustrates a cross-sectional view of an enzyme sensor according to one embodiment of the invention.

A typical enzyme biosensor, e.g., a creatine or creatinine biosensor according to the invention is illustrated in FIG. 1. The enzyme sensor 59 on sensor card 50 includes a three layer composite membrane 60 comprising, arranged from the body fluid sample flow chamber 56 to the electrode 57, an outer diffusion membrane 51 adjacent to the flow channel 56, an enzyme layer 53, located between the outer membrane 51 and an inner membrane 55 that is adjacent to the electrode 57. The enzyme sensor 59 contacts the patient sample as the sample flows along the flow channel 56 and over the outer membrane 51 of the enzyme sensor 59.

In one embodiment of the invention, the steps for making a stable multi-enzyme disaccharide-treated sensor according to the invention include:

(i) solvent casting a plurality of enzymes on an electrode, for example, an optionally cross-linked multi-enzyme mixture, e.g., a three enzyme or a two enzyme mixture, the cross-linker, if applied, selected from the group consisting of glutaraldehyde, 1,4-diisocyanatobutane, 1, 2, 7, 8-diepoxyoctane, 1, 2, 9, 10-diepoxydecane, and combinations thereof; alternatively, immobilization of one or more enzymes on the surface of the electrode can occur by physical absorption, entrapment with a hydrogel, or coated on the electrode by electro-polymerization with conductive monomers, for example. The electrode may be selected from the group consisting of platinum, gold, palladium, alloys of the foregoing, carbon, graphite, and carbon nanotubes;

(ii) applying to the solvent cast multi-enzyme electrode, a diffusion control barrier such as polyurethane, poly(tetrafluoroethylene) ionomers (the perfluorosulfonate ionomer, NAFION®) poly-(2-hydroxymethyl methacrylate), polyvinyl chloride, cellulose acetate, or mixtures and copolymers thereof; followed by, (iii) exposing the solvent cast electrode to a polysaccharide solution, for example, a disaccharide solution, such as, a sucrose solution, or trehalose, raffinose or lactitol in (w/v) concentrations ranging from >0% to 2%, 2% to 25%, 2% to 20%, 5% to 15%, 10% to 15%, preferably, 10% solution for at least 30 minutes to 24 hours, at least 30 minutes to 240 minutes, at least 30 minutes to 120 minutes, at least 30 minutes to 60 minutes, preferably at least 30 minutes, and, (iv) air drying.

In an alternative embodiment of the above described method for making a multi-enzyme poly-saccharide-treated biosensor, as described in greater detail below, rather than exposing the electrode in step (iii) to a polysaccharide solution, polysaccharide and optionally a polyionic compound such as PEI are added directly into the enzyme mixture before solvent casting the enzyme mixture on the electrode, and then the mixture of polysaccharide, optionally, PEI, and multi-enzymes are solvent cast on the electrode.

In yet another alternative embodiment for making a multi-enzyme poly-saccharide-treated biosensor, as described in greater detail below, step (iii) above is combined with the step of adding polysaccharide and, optionally adding a polyionic compound such as PEI directly into the enzyme mixture and then the enzyme mixture is solvent cast on the electrode.

EXEMPLIFICATION OF THE INVENTION

An exemplification of the utility and method of making multi-enzyme biosensors with extended biosensor activity shelf-life and use-life is presented below from studies that were conducted for proof of principle.

Creatinine sensors were fabricated by solvent casting a platinum electrode with a three enzyme mixture. The three enzyme mixture was made with 30% creatininase, 30% creatinase, 30% sarcosine oxidase and 10% glutaraldehyde (percentages by weight) in water. The two enzyme creatine electrode was manufactured by solvent casting a platinum electrode with a two enzyme mixture of 45% creatinase, 45% sarcosine oxidase and 10% glutaraldehyde in water (percentages by weight). The enzyme mixtures are cast on the platinum electrode by dispensing the aqueous enzyme solutions onto the surface of the electrode. The solvent cast enzyme layer on the electrode has a thickness in the range of 1 to 10 microns, preferably 2-5 microns. The enzyme cast electrode was next covered with polyurethane to form the outer membrane. The outer membrane of the electrode is exposed to the patient's body fluid sample that flows in the flow channel of the sensor card.

The outer membrane comprises a blend of polyurethanes having different water uptake levels. A typical composition for one embodiment of the outer membrane is 77% aliphatic, polyether-based polyurethane with 20% water uptake, 17% aliphatic, polyether-based polyurethane with 60% water uptake, and 6% aliphatic, polyether-based polyurethane with 3% water uptake. Alternative polyurethane blends in diffusion barrier outer membranes are also possible such as those described in U.S. Pat. No. 6,960,466 and Outer Membrane Compositions for Creatinine/Creatine Sensors, filed on even-date, each incorporated by reference herein in their entirety for all intents and purposes.

In one embodiment, the outer membrane of the sensor with this composition can be produced, for example, by dispensing a solution of 3.0 mL cyclohexanone solvent, 17.0 mL tetrahydrofuran solvent, 1.08 g of 20% water uptake polyurethane, 0.24 g of 60% water uptake polyurethane and 0.08 g of 3% water uptake polyurethane is layered onto and in direct contact with the enzyme layer of the composite membrane. Other than polyurethane, other suitable polymers include, but are not limited to, poly(tetrafluoroethylene) ionomers (the perfluorosulfonate ionomer, NAFION®), poly-(2-hydroxymethyl methacrylate), polyvinyl chloride, cellulose acetate, and mixtures and copolymers thereof.

Figure 2A:
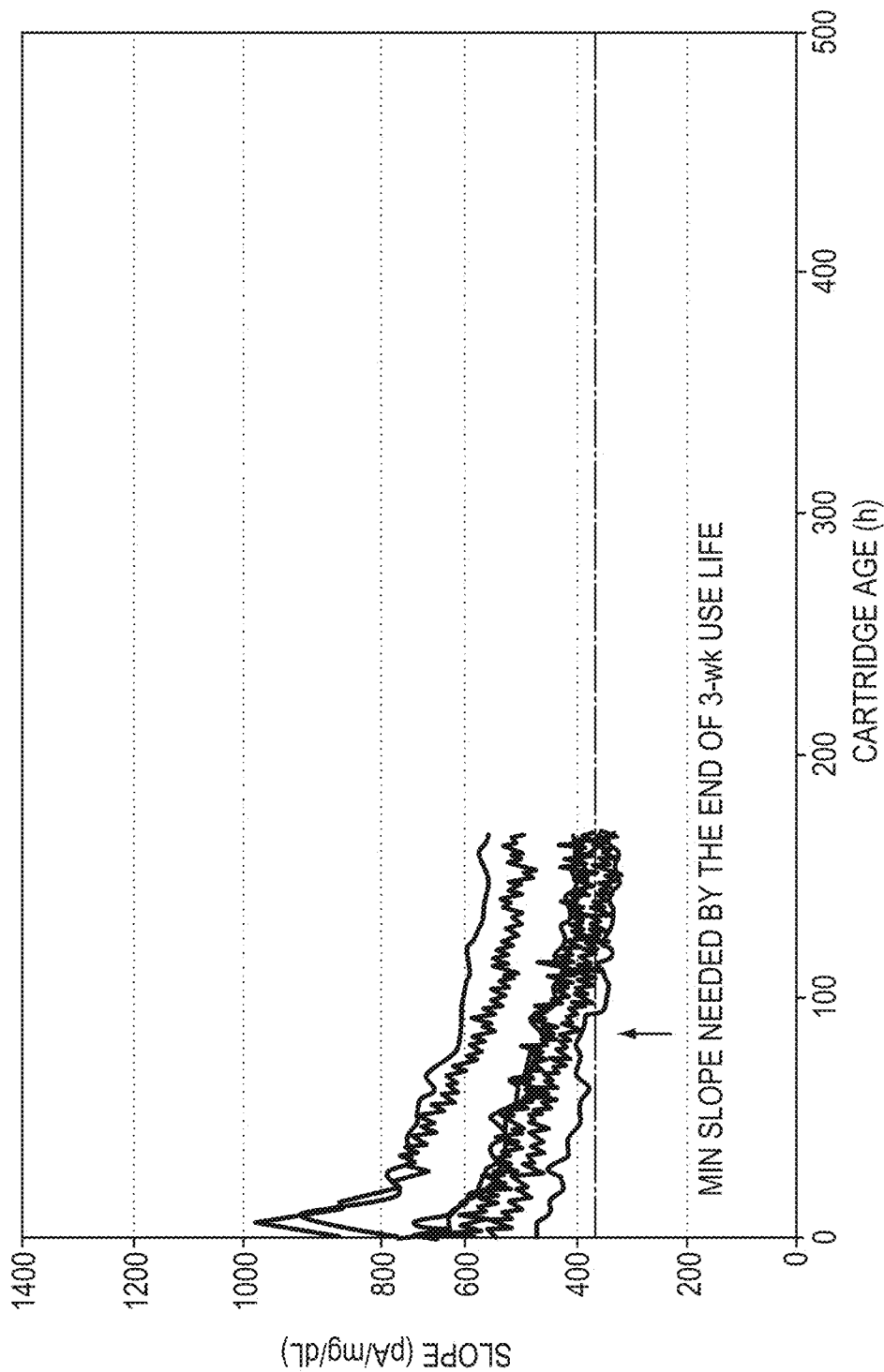
FIG. 2A is a graphic illustration of creatinine sensor activity in a group of 10 cartridges, the activity of the creatinine sensor of each cartridge plotted as slope, in the unit of picoampere/milligram/deciliter (pA/mg/dL) versus age of cartridge (hours), over a three week use period after 5 month room temperature storage, for example, at 22°-25° C. Each cartridge enclosed a creatinine sensor that did not receive sucrose treatment. Testing was discontinued after one week because the slope dropped below the cut-off value of 400 picoampere/milligram/deciliter (400 pA/mg/dL). The cut-off is established to ensure analytical performance consistency from cartridge-to-cartridge (sensor to sensor)

Referring to FIG. 2A, in the conducted studies, some creatinine biosensors (controls) were not sucrose-treated. These creatinine sensors, like the sucrose-treated creatinine biosensors were stored at room temperature.

Figure 2B:
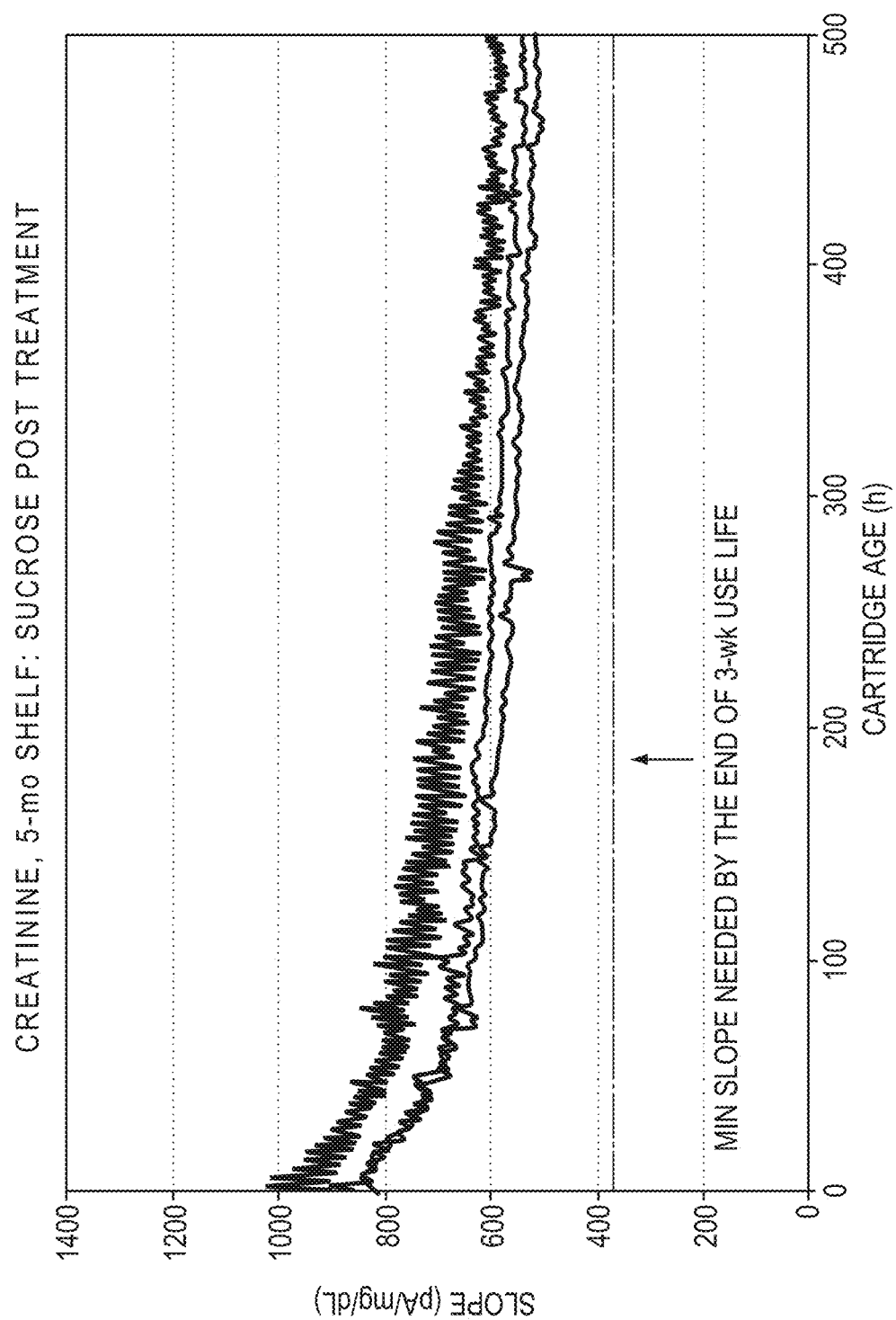
FIG. 2B is a graphic illustration of creatinine sensor activity in another group of 5 cartridges. The activity of the creatinine sensor activity of each cartridge plotted as slope (pA/mg/dL) versus age of cartridge (hours) over a three week use period after 5 month room temperature storage. Each cartridge enclosed a creatinine sensor that received treatment with 10% sucrose.

Referring to FIG. 2B, other creatinine biosensors were immersed in a 10% sucrose solution buffered at biological pH of 7.4 after application of the diffusion barrier, in this case polyurethane, for 30 minutes followed by drying in air at ambient temperature.

Figure 3:
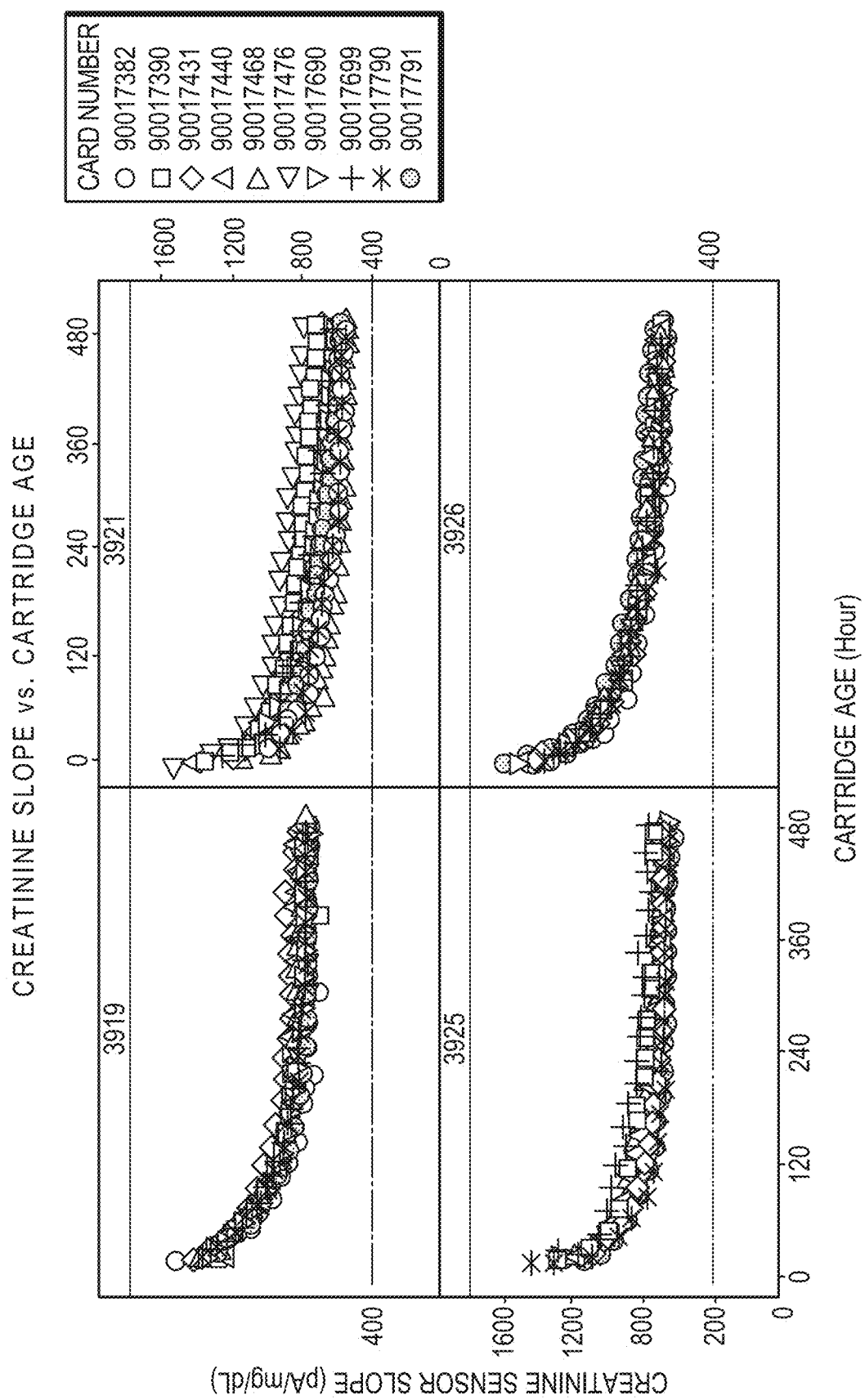
FIG. 3 is a graphic illustration of four batches numbered 3919, 3921, 3925 and 3926, of sucrose-treated and polyethylenimine-containing creatinine sensor sensitivities over a 3 week use-life after 5 month storage at room temperature; a total of twelve creatinine sensors were tested.

Referring to FIG. 3, another group of creatinine sensors were studied by adding polyethylenimine into the three enzyme mixture. These creatinine biosensors were prepared from a mixture of 5% creatininase by weight, 55% creatinase by weight, 30% sarcosine oxidase by weight, 5% PEI by weight and 5% glutaraldehyde by weight, for example. The weight fractions of creatininase, creatinase and sarcosine oxidase in the creatinine electrode and the weight fraction of creatinase and sarcosine oxidase in the creatine electrode can vary and are not limited to the above mentioned percentages by weight. The weight percent of polyethylenimine in creatinine and creatine electrodes can vary, for example, from 1% to 20%, and the weight percent of glutaraldehyde in the creatinine and creatine electrodes can also vary, for example, from 1% to 10%. Polyionic stabilizers, other than polyethylenimine, can also be used for stabilizing the enzyme mixture. Examples of polyionic compounds include but are not limited to poly(N-vinylimidazole), polypropyleneimine, polyallylamine, polyvinylpyridine, polyvinylpyrollidone, polylysine, protamine, and their derivatives. As described in the previous example, a polyurethane outer membrane was then directly applied over the enzyme layer. Then the sensor was exposed to 10% sucrose for at least 30 minutes and followed by drying in the air.

The application of a polysaccharide such as sucrose to extend multi-enzyme biosensor stability is not limited to the sucrose concentrations with or without PEI disclosed in the aforementioned studies. In another embodiment of the invention, following application of the sucrose-containing enzyme mixture onto the electrode, further sucrose treatment, for example, by immersing the electrode with the sucrose containing enzyme mixture already applied to the surface of the electrode, into a solution having various concentrations of sucrose. For example, a three enzyme mixture was made with 6% creatininase, 50% creatinase, 15% sarcosine oxidase, 1% glutaraldehyde, and 28% sucrose (percentages by weight) in water. The creatinine sensor with this sucrose containing enzyme mixture may subsequently undergo additional sucrose treatment again for multiple sucrose treatment after applying the outer membrane as described in the aforementioned examples.

The creatinine biosensors made according to the method described above were stored at room temperature for 5 months. The sensitivity of the two groups of sensors, control creatinine sensors that were not sucrose-treated (FIG. 2A) and sucrose-treated creatinine sensors (FIG. 2B), were studied over a three week period after 5 months of storage at room temperature. The minimum slope (pA/mg/dL) required by the end of the three week use-life was 400 pA/mg/dL.

Referring again to FIG. 2A, studies of the control sensors that were not treated with sucrose were discontinued after one week because the slope of the sensors dropped below the minimum slope threshold (400 pA/mg/dL) required.

Referring again to FIG. 2B, the slope started much higher for the creatinine sensors treated with sucrose and remained above the 400 pA/mg/dL threshold for the duration of the three week study period.

Referring again to FIG. 3, twelve creatinine sensors were selected from four batches (indicated as batch nos. 3919, 3921, 3925, and 3926) three sensors per batch of production sucrose-treated (10% solution) creatinine sensors. These sensors also contained PEI in their enzyme mixture. The sensitivities of the twelve creatinine sensors were studied after 5 months storage and three week use-life. The study demonstrated the consistency of performance among multiple batches of PEI and sucrose-treated creatinine sensors over the three week use-life of the creatinine sensors.

Referring to FIG. 4A, studies of sucrose-treated creatinine sensor analytical performance in measuring creatinine in clinical samples without polyethylenimine in the enzyme mixture were conducted. The difference of creatinine measured between GEM PAK, and a reference chemistry analyzer were plotted vs. plasma creatinine reported by the reference chemistry analyzer, the dashed lines were acceptable limits of bias at any given creatinine concentration for clinical applications. Due to sensor-to-sensor variation in performance, the biases were scattered across wide space and many samples had bias exceeded the acceptable limits (data points outside dashed lines).

Referring to FIG. 4B, studies of sucrose-treated creatinine sensor analytical performance in clinical samples with polyethylenimine-containing enzyme mixture are illustrated. The difference of creatinine measured between GEM PAK and a reference chemistry analyzer were plotted vs. plasma creatinine reported by the reference chemistry analyzer, the dashed lines were acceptable limits of bias at any given creatinine concentration for clinical applications. With modified sensor formulation by the addition of polyethylenimine, the improved sensor performance was demonstrated (data illustrated in FIG. 4B vs. 4A), biases were tightly distributed and most of the samples measured with sensors modified with polyethylenimine had biases within the clinical acceptable limits (data points within dashed lines).

We claim:

1. A biosensor comprising:
an electrode;
a plurality of enzymes immobilized over a surface of the electrode;
a diffusion barrier over the surface of the electrode; and
a polysaccharide;
wherein the diffusion barrier comprises a polymeric compound selected from the group consisting of poly (tetrafluoroethylene) ionomers, the perfluorosulfonate ionomer NAFION®, poly-(2-hydroxymethyl methacrylate), polyvinyl chloride, cellulose acetate, and mixtures and copolymers thereof.

2. The biosensor of claim 1, wherein the electrode comprises platinum, gold, palladium, alloys of platinum, gold and palladium, or carbon.

3. The biosensor of claim 1, wherein the electrode comprises graphite or carbon nanotube.

4. The biosensor of claim 1, wherein said plurality of enzymes are cross-linked.

5. The biosensor of claim 1, wherein the plurality of enzymes comprise creatinase, creatininase, or sarcosine oxidase, and wherein the diffusion barrier comprises a mixture containing polyurethane.

6. The biosensor of claim 1, wherein the polysaccharide comprises sucrose, trehalose, raffinose, or lactitol.

7. The biosensor of claim 1, wherein the biosensor is configured to measure creatine.

8. The biosensor of claim 1, wherein the biosensor is configured to measure creatinine and creatine.

9. The biosensor of claim 1, wherein the polysaccharide comprises 10% sucrose.

10. The biosensor of claim 1, wherein the diffusion barrier is over both the surface of the electrode and the plurality of enzymes.

11. The biosensor of claim 1, wherein the polysaccharide comprises a disaccharide.

12. A method of using a multi-enzyme biosensor, the multi-enzyme biosensor comprising:
an electrode;
a plurality of enzymes immobilized over a surface of the electrode;
a diffusion barrier over the surface of the electrode; and
a polysaccharide;
wherein the diffusion barrier comprises a polymeric compound selected from the group consisting of poly (tetrafluoroethylene) ionomers, the perfluorosulfonate ionomer NAFION®, poly-(2-hydroxymethyl methacrylate), polyvinyl chloride, cellulose acetate, and mixtures and copolymers thereof;
wherein the method comprises using the multi-enzyme biosensor to measure creatine, creatinine, or both creatine and creatinine in a body fluid sample.

13. The method of claim 12, wherein the plurality of enzymes are cross-linked.

14. The method of claim 12, wherein the plurality of enzymes are cross-linked by a chemical comprising glutaraldehyde, 1,4-diisocyanatobutane, 1,2,7,8-diepoxyoctane and 1,2,9,10-diepoxydecane, or a combination thereof.

15. The method of claim 12, wherein the electrode comprises platinum, gold, palladium, alloys of platinum, gold and palladium, or carbon based material.

16. The method of claim 12, wherein the electrode comprises graphite or carbon nanotubes.

17. The method of claim 12, wherein the polysaccharide comprises sucrose, trehalose, raffinose, or lactitol.

18. The method of claim 12, wherein the biosensor measures both creatinine and creatine.

19. The method of claim 12, wherein the biosensor measures creatine only or creatinine only.

20. The method of claim 12, wherein the plurality of enzymes comprises a polyionic compound comprising polyethylenimine, poly(N-vinylimidazole), polypropyleneimine, polyallylamine, polyvinylpiridine, polyvinylpyrollidone, polylysine, protamine, or derivatives of polyionic compounds.

21. The method of claim 12, wherein the electrode is exposed to a polysaccharide solution for at least 30 minutes.

22. The method of claim 12, wherein the biosensor maintains a stable creatinine performance after 5 months of dry storage at ambient temperature and 21 days of use.

23. The method of claim 22, wherein the stable creatinine performance comprises maintaining stable biosensor performance of greater than 400 pA/mg/dL after 5 months storage at ambient temperature and 21 days of use.

24. The method of claim 12, wherein the polysaccharide is added to an enzyme solution before the enzyme solution is applied to the electrode to produce the plurality of enzymes.

25. The method of claim 12, wherein the polysaccharide is applied to the electrode after the diffusion barrier is applied over the surface of the electrode.

26. The method of claim 12, wherein both of the following are required: the polysaccharide is added to an enzyme solution before the enzyme solution is applied to the electrode to produce the plurality of enzymes and the polysaccharide is applied to the electrode after the diffusion barrier is applied to a surface of the plurality of enzymes.

27. The method of claim 12, wherein the polysaccharide comprises 10% sucrose.

28. A disposable cartridge comprising multi-enzyme sensors, where a multi-enzyme sensor among the multi-enzyme sensors comprises:
- an electrode;
- a plurality of enzymes immobilized over a surface of the electrode;
- a diffusion barrier over the surface of the electrode; and
- a polysaccharide;
- wherein the diffusion barrier comprises a polymeric compound selected from the group consisting of poly (tetrafluoroethylene) ionomers, the perfluorosulfonate ionomer NAFION®, poly-(2-hydroxymethyl methacrylate), polyvinyl chloride, cellulose acetate, and mixtures and copolymers thereof.

29. The disposable cartridge of claim 28, wherein the multi-enzyme sensor comprises a creatine sensor.

30. The disposable cartridge of claim 28, wherein the multi-enzyme sensor comprises a creatinine sensor.

31. The disposable cartridge of claim 28, wherein an enzyme among the plurality of enzymes comprises creatininase.

32. The disposable cartridge of claim 28, wherein an enzyme among the plurality of enzymes comprises creatinase.

33. The disposable cartridge of claim 28, wherein an enzyme among the plurality of enzymes comprises sarcosine oxidase.

34. The disposable cartridge of claim 28, further comprising a plurality of sensor arrays and calibration reagents, the plurality of sensor arrays comprising the multi-enzyme sensors.

* * * * *